(12) United States Patent
Greenberg et al.

(10) Patent No.: US 7,232,459 B2
(45) Date of Patent: Jun. 19, 2007

(54) THORACIC AORTIC ANEURYSM STENT GRAFT

(75) Inventors: Roy K. Greenberg, Bratenahl, OH (US); David Ernest Hartley, Subiaco (AU); Erik Edelboe Rasmussen, Slagelse (DK)

(73) Assignees: Cook Incorporated, Bloomington, IN (US); William Cook Europe ApS, Bjaeverskov (DK); William A. Cook Australia Pty. Ltd., Queensland (AU)

( * ) Notice: Subject to any disclaimer, the term of this patent is extended or adjusted under 35 U.S.C. 154(b) by 764 days.

(21) Appl. No.: 10/609,835

(22) Filed: Jun. 30, 2003

(65) Prior Publication Data

US 2004/0106978 A1 Jun. 3, 2004

Related U.S. Application Data

(60) Provisional application No. 60/392,599, filed on Jun. 28, 2002.

(51) Int. Cl.
*A61F 2/06* (2006.01)

(52) U.S. Cl. .................................................. 623/1.13

(58) Field of Classification Search ............... 623/1.11, 623/1.12, 1.13, 1.16, 1.2, 1.23, 1.36; 606/191–198
See application file for complete search history.

(56) References Cited

U.S. PATENT DOCUMENTS

| 5,387,235 | A | 2/1995 | Chuter |
| 5,720,776 | A | 2/1998 | Chuter et al. |
| 5,851,228 | A * | 12/1998 | Pinheiro ..................... 623/1.13 |
| 6,206,931 | B1 | 3/2001 | Cook et al. |
| 6,331,191 | B1 * | 12/2001 | Chobotov .................. 623/1.44 |
| 6,355,056 | B1 | 3/2002 | Pinheiro |
| 6,641,606 | B2 * | 11/2003 | Ouriel et al. .............. 623/1.12 |
| 6,939,370 | B2 | 9/2005 | Hartley et al. |
| 2003/0120332 | A1 | 6/2003 | Hartley |
| 2003/0233140 | A1 | 12/2003 | Hartley et al. |
| 2004/0054396 | A1 | 3/2004 | Hartley et al. |
| 2004/0073289 | A1 | 4/2004 | Hartley |

FOREIGN PATENT DOCUMENTS

| WO | 9853761 | 12/1998 |
| WO | 9929262 | 3/1999 |
| WO | 0167993 | 9/2001 |
| WO | 03034948 | 5/2003 |

OTHER PUBLICATIONS

International Search Report; PCT/US03/20642; Oct. 2003.

* cited by examiner

*Primary Examiner*—Kevin T. Truong
(74) *Attorney, Agent, or Firm*—Richard J. Godlewski

(57) ABSTRACT

A thoracic stent graft (20) has a tubular bio-compatible graft material body (22) with a lumen therethrough with a proximal end (26) and a distal end (27). There is a sealing stent (28) at the proximal end of the tubular body with an anchoring device which may be a barb (30) affixed to the sealing stent. A distal attachment stent (34) with barbs (36) can be affixed to and extend from the distal end (27) of the graft material body. Intermediate stents (24) are provided along the length of the body. The thoracic stent graft can be in one or two portions.

15 Claims, 5 Drawing Sheets

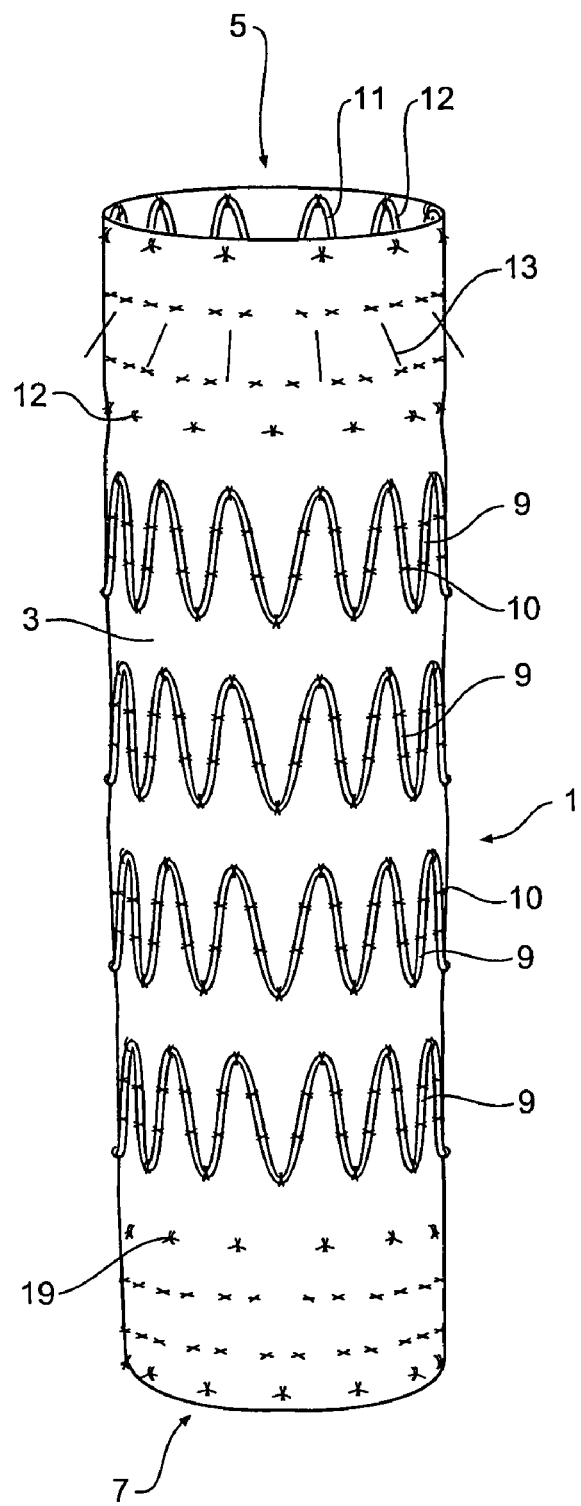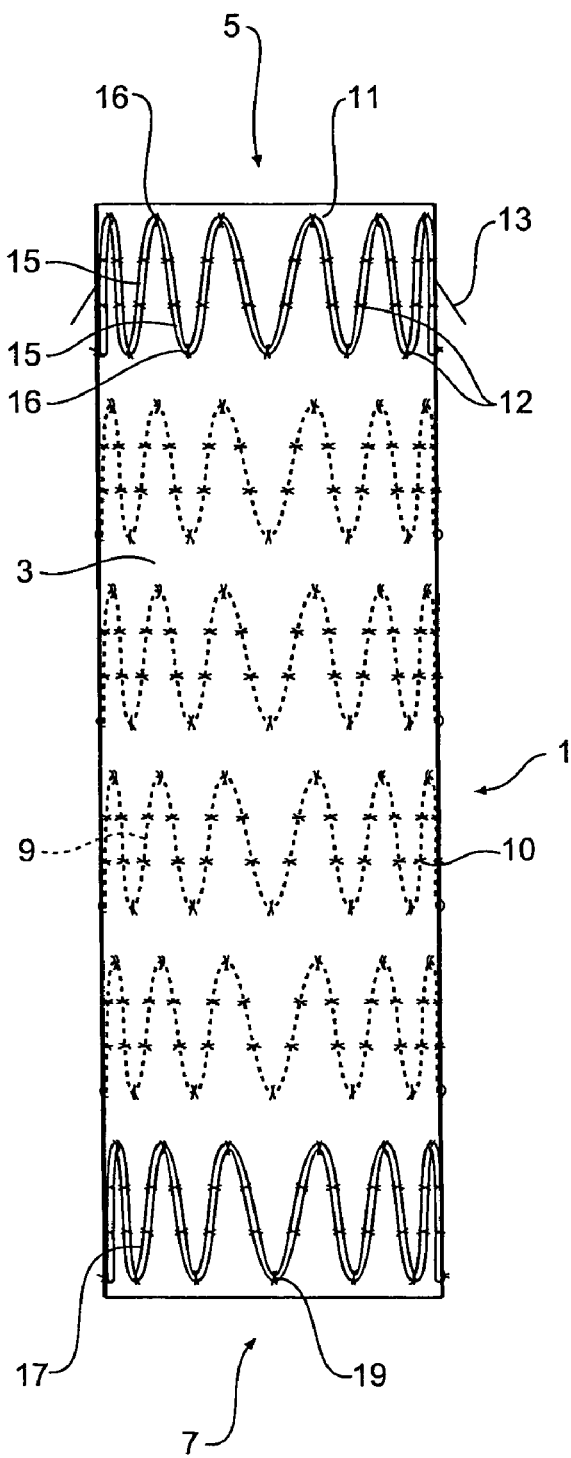
Fig 1                                   Fig 2

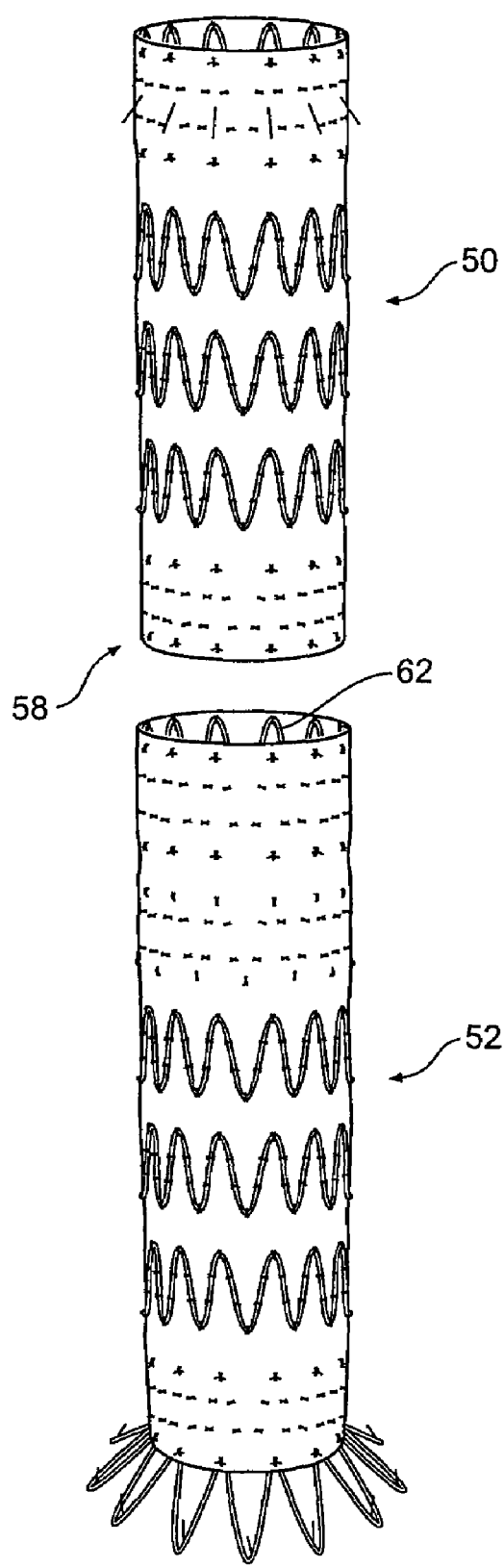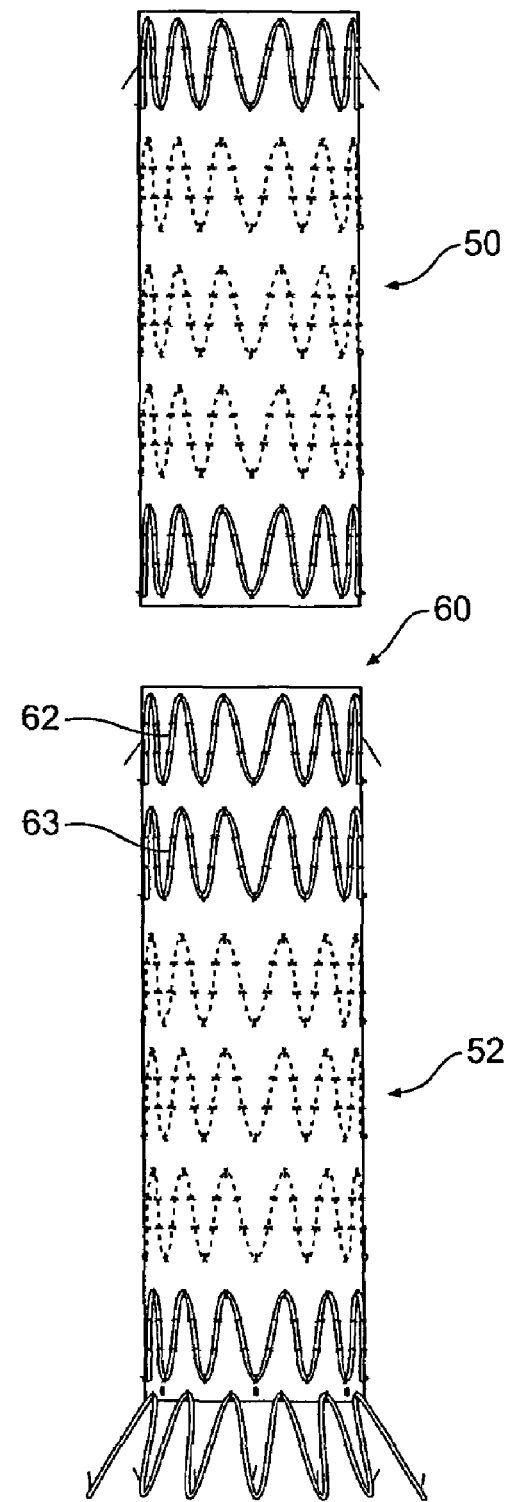
Fig 5
Fig 6

THORACIC AORTIC ANEURYSM STENT GRAFT

CROSS-REFERENCE TO RELATED APPLICATIONS

This application claims priority of provisional application Ser. No. 60/392,599, filed Jun. 28, 2002.

TECHNICAL FIELD

This invention relates to the field of medical devices and more particularly to vascular devices.

BACKGROUND OF THE INVENTION

Throughout this specification the term distal with respect to a portion of the aorta, a deployment device or a prosthesis is intended to refer to the end of the aorta, deployment device or prosthesis further away in the direction of blood flow away from the heart and the term proximal is intended to refer to the portion of the aorta, deployment device or end of the prosthesis nearer to the heart. When applied to other vessels corresponding terms such as caudal and cranial should be understood.

In recent years, endovascular implantable devices have been developed for treatment of aortic aneurysms, wherein the devices are delivered to the treatment site through the vascular system of the patient rather than by open surgery. Such devices generally include a tubular or cylindrical frame work or scaffolding of one or more stents to which is secured a tubular shape of graft material such as woven DACRON polyester (trade mark of E I Dupont de Nemours and Co.), polytetrafluoroethylene (PTFE) and the like. These devices are initially reduced to a small diameter and placed into the leading or proximal end of a catheter delivery system. The delivery system is inserted into the vascular system of the patient such as through a femoral incision. The leading end of the delivery system is maneuvered to the treatment site over a previously positioned guide wire. Through manipulation of control systems that extends to the proximal end of the catheter from the distal end of the system outside the patient, the device is then deployed by holding the device at its location and withdrawing the surrounding sheath, whereafter the stent graft self expands or is expanded through use of a balloon therewith that is expanded. The stent graft becomes anchored in position to healthy vessel wall tissue in the aorta such as by barbs, whereafter the delivery system is then removed leaving the device in position traversing the aneurysm in a manner that channels all blood flow through the stent graft so that no blood flow enters the aneurysm thereafter, such that not only does the aneurysm no longer continue to grow and possibly rupture but the aneurysm actually beings to shrink and commonly disappears entirely.

For treatment of abdominal aortic aneurysms in particular, bifurcated stent grafts are known wherein a pair of leg sections extend from the end of the stent graft and are disposed in the iliac arteries in the bifurcation of the aorta and iliac arteries, while the opposite end of the stent graft is anchored to the aorta wall adjacent to the renal arteries, usually by means of an attachment stent having barbs that penetrate harmlessly into the vessel wall so that blood flow does not displace the stent graft from its precise location. One such bifurcation stent graft is the ZENITH AAA stent graft sold by William A. Cook Australia Pty Ltd., Brisbane, Queensland, Australia.

Another example of such a stent graft is disclosed in PCT Publication No. WO 98/53761 in which the stent graft includes a sleeve or tube of biocompatible graft material defining a lumen, and further includes several stents secured therealong, with the stent graft spanning the aneurysm extending along the aorta proximally (ie towards the heart) from the two iliac arteries. The reference also discloses the manner of deploying the stent graft in the patient utilizing an introducer assembly. The graft material-covered portion of the single-lumen proximal end of the stent graft bears against the wall of the aorta above the aneurysm to seal the aneurysm at a location that is spaced distally (ie away from the heart) of the entrances to the renal arteries. Thin wire struts of a proximal stent extension traverse the renal artery entrances without occluding them, since no graft material is utilized along that portion of the proximal stent, while securing the stent graft in position within the aorta when the stent graft self-expands. An extension is affixed to one of the legs of the stent graft to extend along a respective iliac artery and, optionally, extensions may be affixed to both legs.

However, for an aneurysm that develops in the thoracic arch of the aorta, stent grafts are needed that are deployable to extend along the substantial curvature of the arch without occluding the main branch vessels joined to the aorta along the arch's curve, all of which may be involved in and compromised by the aneurysm.

SUMMARY OF THE INVENTION

The foregoing problems are solved and a technical advance is achieved by a thoracic stent graft having a tubular biocompatible graft material body with a lumen therethrough and having a proximal end and a distal end, a sealing stent at the proximal end of the tubular body and an anchoring device affixed to the sealing stent.

Preferably the sealing stent is inside the graft material body and the anchoring device extends from the sealing stent and through the graft material body.

Preferably the anchoring device extends towards a distal end of the tubular body.

The anchoring device can comprise a plurality of barbs extending distally.

There can be further included a distal attachment stent affixed to and extending from the distal end of the graft material body and the distal attachment stent can include at least one anchoring device affixed thereto and extending proximally. The at least one anchoring device can be a barb.

There can be further included one or more intermediate stents positioned between the proximal sealing stent and the distal end and at least some of the one or more of the intermediate stents can be on the outside surface of the tubular body.

Preferably the stents are self-expanding stents such as zigzag self-expanding Z stents.

Preferably the intermediate stents are spaced apart from five to ten millimeters to allow for bending of the stent graft.

The graft material can be selected from polyester, expanded polytetrafluoroethylene (ePTFE) or extra-cellular matrix.

The tubular body can have a length of from 75 to 240 mm and a diameter of from 22 to 42 mm. The tubular body can be substantially cylindrical or have a tapered shape with a different diameter at each end.

In one embodiment the tubular graft body comprises a first portion and a second portion, the first portion including the sealing stent and the second portion including the distal attachment stent. The first portion can include at least one internal sealing stent at its distal end and the second portion can include at least two internal sealing stents at its proximal end. Preferably the first portion and the second portion have respective lengths to provide at least an overlap of two sealing stents. The first portion and the second portion when assembled together can have a combined length in use of from 150 to 350 mm and a diameter of from 22 to 42 mm.

In a further form, the invention is said to reside in a thoracic stent graft having a tubular biocompatible graft material body with a lumen therethrough and having a proximal end and a distal end, a sealing stent at the proximal end of the tubular body, a proximal anchoring device affixed to the sealing stent and a distal attachment stent affixed to and extending from the distal end of the graft material body.

In a still further form, the invention is said to reside in a thoracic stent graft assembly having a proximal first portion and a distal second portion, each of the proximal first portion and distal second portion having a tubular biocompatible graft material body with a lumen therethrough and having a proximal end and a distal end, a sealing stent at the proximal end of the first proximal portion and a proximal anchoring device affixed to the sealing stent and a distal attachment stent affixed to and extending from the distal end of the distal second portion.

BRIEF DESCRIPTION OF THE DRAWING

This, then, generally describes the invention, but to assist with understanding, reference will now be made to the accompanying drawings which show preferred embodiments of the invention.

In the drawings:

FIG. 1 shows a first embodiment of stent graft according to the invention;

FIG. 2 shows a cross-sectional view of the stent graft of FIG. 1;

FIG. 5 shows a third embodiment of a stent graft according to this invention;

FIG. 6 shows a cross-sectional view of the stent graft shown in FIG. 5;

DETAILED DESCRIPTION

Figure 3:
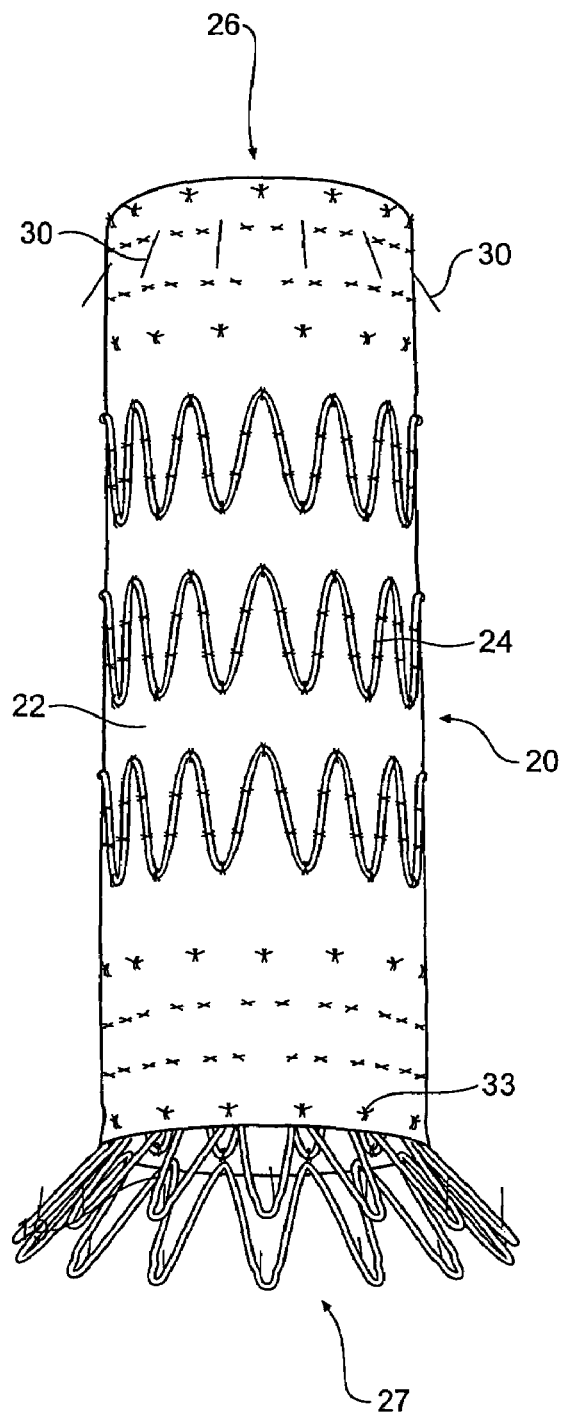
FIG. 3 shows a second embodiment of the stent graft according to the invention.

U.S. Pat. No. 5,387,235 entitled "Expandable Transluminal Graft Prosthesis For Repair Of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

PCT Patent Publication No. WO 99/29262 entitled "Endoluminal Aortic Stents" discloses a fenestrated prosthesis for placement where there are intersecting arteries. This feature and other features disclosed in PCT Patent Publication No. WO 99/29262 could be used with the present invention and the disclosure of PCT Patent Publication No. WO 99/29262 is herewith incorporated in its entirety into this specification.

PCT Patent Publication No. WO 03/034948 entitled "Prosthesis For Curved Lumens" discloses prostheses with arrangements for bending the prosthesis for placement into curved lumens. This feature and other features disclosed in PCT Patent Publication No. WO 03/034948 could be used with the present invention and the disclosure of PCT Patent Publication No. WO 03/034948 is herewith incorporated in its entirety into this specification.

U.S. Provisional Patent Application Ser. No. 60/392,682, filed Jun. 28, 2002, entitled "Trigger Wires" discloses release wire systems for the release of stent grafts retained on introducer devices. This feature and other features disclosed in U.S. Provisional Patent Application Ser. No. 60/392,682 could be used with the present invention and the disclosure of U.S. Provisional Patent Application Ser. No. 60/392,682 is herewith incorporated in its entirety into this specification.

U.S. Provisional Patent Application Ser. No. 60/392,667, filed Jun. 28, 2002, entitled "Thoracic Deployment Device" discloses introducer devices adapted for deployment of stent grafts particularly in the thoracic arch. This feature and other features disclosed in U.S. Provisional Patent Application Ser. No. 60/392,667 could be used with the present invention and the disclosure of U.S. Provisional Patent Application Ser. No. 60/392,667 is herewith incorporated in its entirety into this specification.

U.S. Provisional Patent Application Ser. No. 60/392,599, filed Jun. 28, 2002, entitled "Thoracic Aortic Aneurysm Stent Graft" discloses stent grafts that are useful in treating aortic aneurysms particularly in the thoracic arch. This feature and other features disclosed in U.S. Provisional Patent Application Ser. No. 60/392,599 could be used with the present invention, and the disclosure is herewith incorporated in its entirety into this specification.

U.S. Provisional Patent Application Ser. No. 60/391,737, filed Jun. 26, 2002, entitled "Stent-Graft Fastening Arrangement" discloses arrangements for fastening stents onto grafts particularly for exposed stents. This feature and other features disclosed in U.S. Provisional Patent Application No. 60/391,737 could be used with the present invention and the disclosure of U.S. Provisional Patent Application Ser. No. 60/391,737 is herewith incorporated in its entirety into this specification.

U.S. Provisional Patent Application Ser. No. 60/405,367, filed Aug. 23, 2002, entitled "Asymmetric Stent Graft Attachment" discloses retention arrangements for retaining onto and releasing prostheses from introducer devices. This feature and other features disclosed in U.S. Provisional Patent Application Ser. No. 60/405,367 could be used with the present invention and the disclosure of U.S. Provisional Patent Application Ser. No. 60/405,367 is herewith incorporated in its entirety into this specification.

U.S. Provisional patent application Ser. No. 10/322,862, filed Dec. 18, 2002, entitled "Stent Graft With Improved Adhesion" discloses arrangements on stent grafts for enhancing the adhesion of such stent grafts into walls of vessels in which they are deployed. This feature and other features disclosed in U.S. Provisional patent application Ser. No. 10/322,862 could be used with the present invention and the disclosure of U.S. Provisional patent application Ser. No. 10/322,862 is herewith incorporated in its entirety into this specification.

Now looking more closely at the drawings and in particular FIGS. 1 and 2 showing external and internal views of a first embodiment of the present invention, it will be seen that a stent graft 1 includes a tubular body 3 formed from a biocompatible woven or non-woven fabric or other material. The tubular body has a proximal end 5 and a distal end 7. The tubular body may have a diameter in the range of 22 to 42 mm and a length of from 100 to 150 mm. The stent graft 1 may be tapered, outwardly bulging like a balloon or of constant diameter along its length depending upon the topography of the vasculature.

Along the length of the tubular body, there are a number of self-expanding zigzag stents 9 such as the well-known Gianturco Z or zigzag stent on the outside of the body. In this embodiment there are four external stents 9 spaced apart by a distance of between 5 to 10 mm. The external stents 9 are joined to the graft material by means of stitching 10 preferably using a monofilament or braided suture material.

At the proximal end 5 of the stent graft 1 there is provided an internal zigzag stent 11 which provides a sealing function for the proximal end of the stent graft. The outer surface of the tubular body 3 at the proximal end 5 presents an essentially smooth outer surface which with the assistance of the internal zigzag stent 11 can engage and seal against the wall of the aorta when it expands and is deployed. The proximal stent 11 is comprised of struts 15 with bends 16 at each end of the struts. Affixed to some of the struts 15 are barbs 13 which extend distally from the struts through the graft material. When the stent graft is deployed into a thoracic arch, the barbs 13 engage and/or penetrate into the wall of the aorta and prevent distal movement of the stent graft caused by pulsating blood flow through the stent graft.

It will be noted that the stent 11 is joined to the graft material by means of stitching 12 preferably using a monofilament or braided suture material.

At the distal end 7 of the stent graft 1, there is an internal sealing stent 17 (see FIG. 2) which again is fastened to the graft material body 3 by stitching 19 preferably using a monofilament or braided suture material. The outer surface of the tubular body 3 at the distal end 7 presents an essentially smooth outer surface which with the assistance of the internal zigzag stent 17 can engage and seal against the wall of the aorta when it is deployed.

The stent graft shown in FIGS. 1 and 2 may be used for treatment of patients with symptomatic acute or chronic dissections and ruptures in the descending thoracic aorta.

Figure 4:
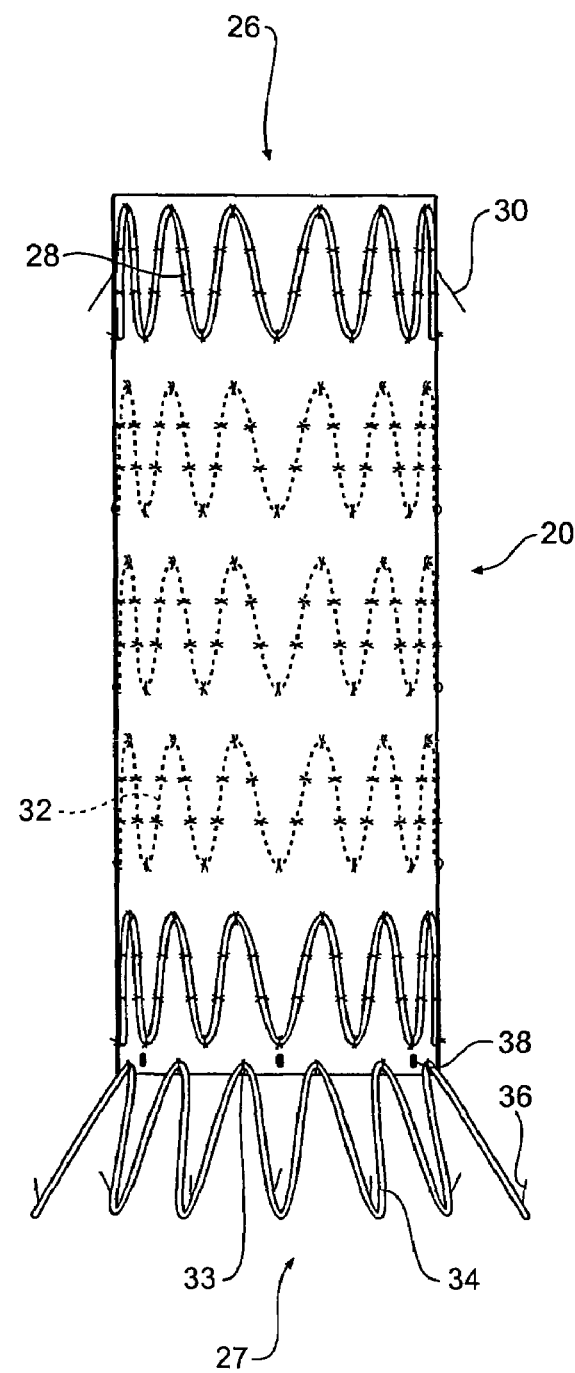
FIG. 4 shows a cross-sectional view of the stent graft shown in FIG. 3.

FIGS. 3 and 4 show external and internal views of a second embodiment of the stent graft according to the present invention. In this embodiment, the stent graft 20 has a tubular graft material body 22 in the same manner as the embodiment shown in FIG. 1 with external stents 24 spaced along the body with a longitudinal spacing of approximately 5 to 10 mm between the stents. The length of the stent graft may be in the range of 75 to 241 mm and a diameter in the range of 22 to 42 mm in 2 mm increments.

Also in a similar manner to the embodiment shown in FIGS. 1 and 2 at the proximal end 26 of the stent graft there is an internal sealing stent 28 with barbs 30.

At the distal end 27 of the stent graft 20, there is also an internal distal sealing stent 32 but in addition, there is a distally extending exposed zigzag stent 34. This distally extending exposed stent 34 has barbs 36 on some of its struts and these barbs 36 are directed proximally. The distally extending exposed zigzag stent 34 is fastened to the tubular graft material body 22 by stitching 33.

It will be noted that there are provided at the distal end of the stent graft radiographic markers 38 to enable correct positioning of the distal end of the stent graft.

Hence, when the stent graft according to this embodiment of the invention is deployed, the barbs 30 prevent distal migration of the proximal end of the stent graft and the barbs 36 on the exposed stent 34 prevent proximal migration of the distal end of the stent graft 20. This tendency of distal migration of the distal end and proximal migration of the distal end may occur if the central portion of the stent graft is free within an aneurysm and sideways force on a curved stent graft caused by pulsating blood flow causes sideways movement of the body of the stent graft with the potential for distal movement of the proximal end and proximal movement of the distal end.

The stent graft shown in FIGS. 3 and 4 may be used for endovascular repair of thoracic aortic aneurysms in the descending thoracic aorta and particularly for treatment of patients with atherosclerotic aneurysms, symptomatic acute or chronic dissections, contained ruptures and growing aneurysms, which result in distal ischaemia.

FIGS. 5 and 6 show external and internal views of a third embodiment of the stent graft according to the present invention. In this embodiment, a thoracic stent graft assembly is formed from a first portion 50 and a second portion 52. The first portion 50 is intended to be deployed proximally of the second portion 52. The first portion 50 is substantially identical with the stent graft embodiment shown in FIGS. 1 and 2. It has proximal and distal internal sealing stents in a tubular graft body, barbs extending from the proximal sealing stent and external zigzag stents between the proximal and distal sealing stents.

The second portion 52 is substantially the same as the embodiment shown in FIGS. 3 and 4 except that there are two internal sealing stents 62, 63 at the proximal end 60 of the second portion 52. It will be noted that although the second portion 52 is substantially similar to the embodiment shown in FIGS. 3 and 4 it does not include the distally extending anchoring barbs on the proximal sealing stent 62.

The proximal end 60 of the second portion 52 with the internal sealing stents 62, 63 can be deployed either inside the distal end 58 of the first portion 50 or outside the distal end 58 of the first portion 50.

This means that in deploying the stent graft assembly of this embodiment of the invention either the first or second portions may be deployed first and the other portion subsequently deployed depending upon the requirements in a particular case.

In either case it is preferable to have at least two stents overlap and it may be noted that by having this overlap there is at least one stent length of smooth internal surface of one of the portions engaging against a smooth external surface of the other of the portions. By this arrangement, sealing between the first and second portions is possible. Also, by having an overlap of at least two stents, relative movement between the first and second portions is less likely to cause parting of the first and second portions of the thoracic stent graft assembly when it is deployed and pulsating blood flow through the stent graft causes sideways movement of the centre portion of the stent graft as discussed above.

The stent graft shown in FIGS. 5 and 6 may be used for endovascular repair of thoracic aortic aneurysms in the descending thoracic aorta and particularly for treatment of patients with atherosclerotic aneurysms, symptomatic acute or chronic dissections, contained ruptures and growing aneurysms. The ability to adjust the overall length of the device by providing more or less overlap of the first and second portions (i.e. "tromboning") allows more accurate placement of the proximal and distal sealing stents and the anchoring barbs.

Figure 7:
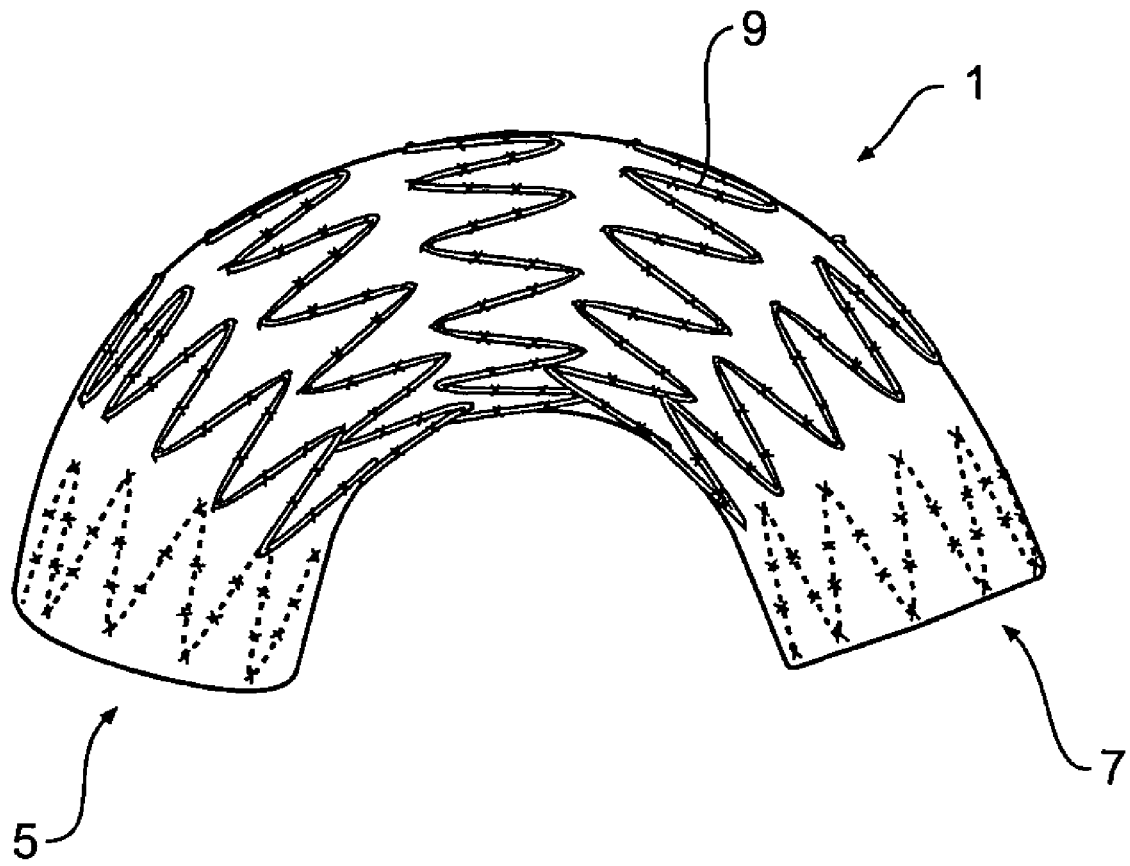
FIG. 7 shows the stent graft of one embodiment of the invention flexed to fit around the thoracic arch.

FIG. 7 shows a stent graft of the embodiment shown in FIG. 1 to show the amount of bending which is possible in the stent graft for placement in the thoracic arch of a patient. The internal radius of curvature of the stent graft according to this invention may be any radius greater than 35 mm. This can be achieved by having the stents longitudinally spaced apart by between five to ten millimeters as discussed earlier and so far as possible staggering the placement of apices of adjacent stents. This may not be possible where adjacent stents have different numbers of struts.

Figure 8:
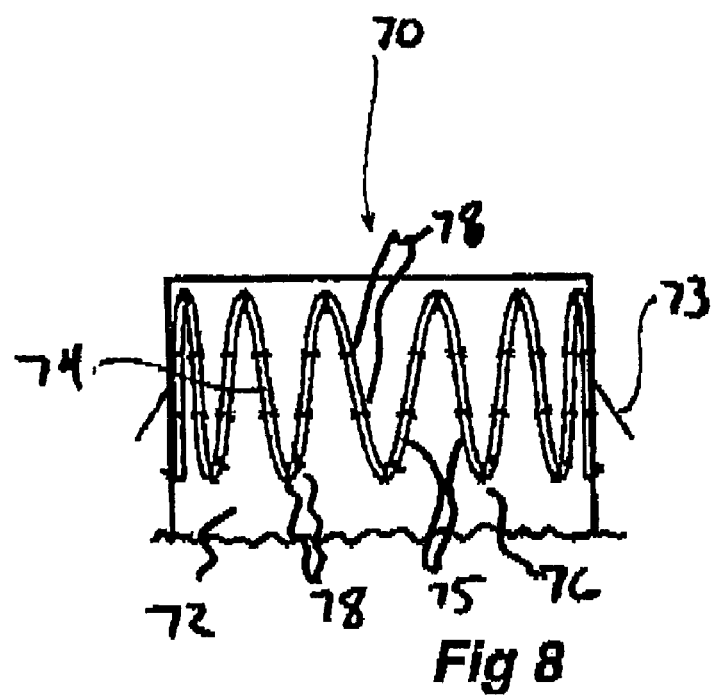
FIG. 8 shows a cross-sectional view of the proximal end of a stent graft showing a sealing stent.

FIG. 8 shows features of a sealing stent that may be present in any of the above embodiments. A stent graft 70 has a graft material body 72 and an internal sealing stent 74 joined to the graft material by stitching 78, also referred to as fastenings. Stent 74 is a zigzag stent having struts 75 with bends 76 at each end of the struts. Affixed to at least some of the struts 75 are barbs 73 which extend distally from the struts through the graft material.

As described in U.S. Provisional Patent Application Ser. No. 60/391,737, which has been incorporated herein by reference, where the stent graft is deployed in a blood vessel, blood flow causes a pull on the graft material tube which is resisted by the barbs on the stent. Hence the fastenings of the stent joining the stent to the graft material take the pull on the prosthesis, and these fastenings preferably are sufficiently strong to take that pull. Similarly, the barbs on the exposed stent used on the distal end of the graft material tube resist blood flow pull on the graft material tube.

Figure 9:
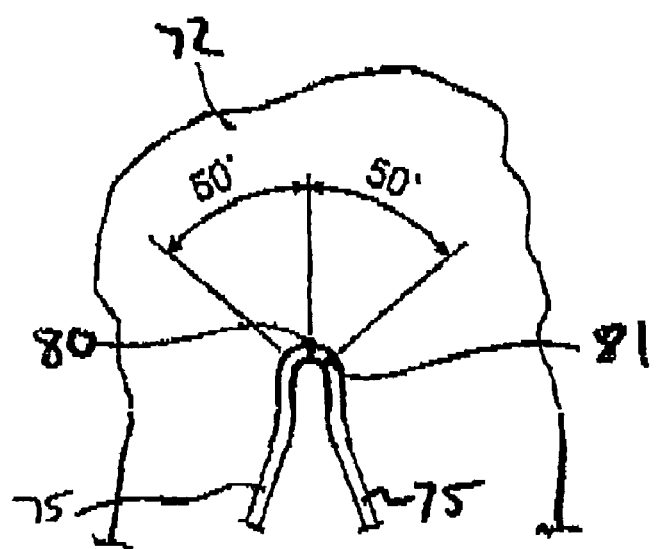
FIG. 9 shows further detail of the fastening shown in FIG. 8.

FIG. 9 shows features of a distally extending exposed zigzag stent used in the embodiments shown in FIGS. 3 to 6. As can be seen in the detailed views in FIG. 9, the struts 79 and bend 82 of the stent are on the inside of the graft material 72. At least two fastenings 80 and 81 are used to fasten the stent 83 to the graft material 72. As shown here, the first fastening 80 is positioned at the apex of the bend 82, and a second fastening 81 is positioned spaced apart adjacent the transition from the bend 82 to the struts 79 of the stent. The second fastening 81 can be positioned on either strut 79 extending from the bend 82 in a region extending up to an angle of 50° either side of the first fastening 80 measured around the radius of the bend from the apex of the bend 82. Generally the second fastening 81 is spaced from the first fastening 80 by 0.5 to 2 mm.

The spaced apart fastenings are preferably present at the proximal bends of the distally extending stent 34 of FIGS. 3 and 4, and the distally extending stent of FIGS. 5 and 6.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A thoracic stent graft having a tubular bio-compatible graft material body with a lumen therethrough and having a proximal end and a distal end, the stent graft comprising an internal proximal sealing stent at the proximal end thereof and a proximal anchoring device affixed to the sealing stent, the anchoring device extending from the sealing stent and through the graft material body towards the distal end of the, the anchoring device comprising a plurality of barbs extending distally, one or more intermediate stents positioned on the outside surface of the tubular body between the proximal sealing stent and the distal end on the outside of the tubular body, the intermediate stents being spaced apart by from five to ten millimeters to allow for bending of the stent graft and an internal distal sealing stent.

2. A thoracic stent graft as in claim 1 further including a distal attachment stent affixed to and extending from the distal end of the graft material body.

3. A thoracic stent graft as in claim 2 wherein the distal attachment stent includes at least one distal anchoring device affixed thereto and extending proximally.

4. A thoracic stent graft as in claim 3 wherein the at least one distal anchoring device is a barb.

5. A thoracic stent graft as in claim 2 wherein the tubular graft body comprises a first portion and a second portion, the first portion including the internal proximal sealing stern and the second portion including the distal attachment stent.

6. A thoracic stent graft as in claim 5 wherein the second portion comprises two internal sealing stents at the proximal end thereof, one or more intermediate stents positioned on the outside surface of the tubular body between the internal sealing stents and the distal end of the second portion on the outside of the tubular body and the internal distal sealing stent and the distal attachment stent affixed to and extending from the distal end of the second portion.

7. A thoracic stent graft as in claim 5 wherein the first portion and the second portion have respective lengths to provide when assembled together at least an overlap of two sealing stents.

8. A thoracic stent graft as in claim 5 wherein the first portion and the second portion when assembled together to provide at least an overlap of two sealing stents have a combined length in use of from 150 to 350 mm and a diameter of from 22 to 42 mm.

9. A thoracic stent graft as in claim 1 wherein the scents are zigzag self expanding sterns.

10. A thoracic stent graft as in claim 1 wherein the graft material is selected from at least one of polyester, expanded polyretrafluoroethylene or extra-cellular matrix.

11. A thoracic stent graft as in claim 1 wherein the tubular body has a length of from 75 to 240 mm and a diameter of from 22 to 42 mm.

12. A thoracic stent graft comprising a tubular biocompatible graft material body with a lumen therethrough and a proximal end and a distal end, an internal proximal sealing stent at the proximal end thereof and a proximal anchoring device affixed to the sealing stent, the anchoring device extending from the sealing stent and through the graft material body towards the distal end of the, the anchoring device comprising a plurality of barbs extending distally, one or more intermediate stents positioned on the outside surface of the tubular body between the proximal sealing stent and the distal end, the intermediate stents being spaced apart by from five to ten millimeters to allow for bending of the stent graft and an internal distal sealing stent and an internal distal sealing stent and a distal attachment stent affixed to and extending from the distal end, the distal attachment stent including at least one anchoring device affixed thereto and extending proximally.

13. A thoracic stent graft assembly having a proximal first portion and a distal second portion, each of the proximal first portion and distal second portion having a tubular biocompatible graft material body with a lumen therethrough and having a proximal end and a distal end, the proximal first portion comprising an internal proximal sealing stent at the proximal end thereof and a proximal anchoring device affixed to the sealing stent, the anchoring device extending from the sealing stent and through the graft material body towards the distal end of the first portion, the anchoring device comprising a plurality of barbs extending distally, one or more intermediate stents positioned on the outside surface of the tubular body between the proximal sealing stent and the distal end of the first portion on the outside of the tubular body, the intermediate stents being spaced apart by from five to ten millimeters to allow for bending of the stent graft and an internal distal sealing stent, the distal second portion comprising two internal sealing stents at the proximal end thereof, one or more intermediate stents positioned on the outside surface of the tubular body between the internal sealing stents and the distal end of the second portion on the outside of the tubular body, the intermediate stents being spaced apart by from five to ten millimeters to allow for bending of the stent graft and an internal distal sealing stent and a distal attachment stent affixed to and extending from the distal end of the distal second portion the distal attachment stent including at least one anchoring device affixed thereto and extending proximally.

14. A thoracic stent graft assembly as in claim 13 wherein the first portion and the second portion when assembled together to provide at least an overlap of two sealing stents have a combined length in use of from 150 to 350 mm and a diameter of from 22 to 42 mm.

15. A thoracic stent graft assembly as in claim 13 wherein the graft material of each of the proximal first portion and distal second portion is selected from at least one of polyester, expanded polytetrafluoroethylene or extra-cellular matrix.

* * * * *

UNITED STATES PATENT AND TRADEMARK OFFICE
CERTIFICATE OF CORRECTION

PATENT NO. : 7,232,459 B2
APPLICATION NO. : 10/609835
DATED : June 19, 2007
INVENTOR(S) : Greenberg et al.

It is certified that error appears in the above-identified patent and that said Letters Patent is hereby corrected as shown below:

In Column 8, line 26, after "the," please insert --tubular bio-compatible graft material body--.

In Column 8, line 44, please delete "stern" and insert in lieu thereof --stent--.

In Column 8, line 63, please delete "scents" and insert in lieu thereof --stents--.

In Column 8, line 64, please delete "sterns" and insert in lieu thereof --stents--.

In Column 8, line 67, please delete "polyretrafluoroethylene" and insert in lieu thereof --polytetrafluoroethylene--.

In Column 9, line 4, please delete "blo" and insert in lieu thereof --bio--.

In Column 9, line 10, after "the," please insert --tubular bio-compatible graft material body--.

Signed and Sealed this

Ninth Day of February, 2010

David J. Kappos
*Director of the United States Patent and Trademark Office*